United States Patent
Abbondanza et al.

(10) Patent No.: US 12,279,526 B2
(45) Date of Patent: Apr. 15, 2025

(54) DISUBSTITUTED FLUOROARYLOXYBENZO-HETERODIAZOLE COMPOUNDS

(71) Applicant: ENI S.P.A., Rome (IT)

(72) Inventors: Luigi Abbondanza, Novara (IT); Antonio Alfonso Proto, Novara (IT); Giuliana Schimperna, Novara (IT)

(73) Assignee: ENI S.P.A., Rome (IT)

( * ) Notice: Subject to any disclaimer, the term of this patent is extended or adjusted under 35 U.S.C. 154(b) by 850 days.

(21) Appl. No.: 17/441,513

(22) PCT Filed: Mar. 19, 2020

(86) PCT No.: PCT/IB2020/052548
§ 371 (c)(1),
(2) Date: Sep. 21, 2021

(87) PCT Pub. No.: WO2020/194147
PCT Pub. Date: Oct. 1, 2020

(65) Prior Publication Data
US 2022/0165959 A1    May 26, 2022

(30) Foreign Application Priority Data
Mar. 22, 2019  (IT) .......... 102019000004161

(51) Int. Cl.
*C07D 417/14*    (2006.01)
*H10K 85/60*    (2023.01)
*H10K 30/00*    (2023.01)

(52) U.S. Cl.
CPC ......... *H10K 85/657* (2023.02); *C07D 417/14* (2013.01); *H10K 85/6576* (2023.02); *H10K 30/00* (2023.02)

(58) Field of Classification Search
CPC ............... C07D 417/14; H10K 85/657; H10K 85/6576; H10K 30/00
See application file for complete search history.

(56) References Cited

U.S. PATENT DOCUMENTS

2017/0342087 A1* 11/2017 Bianchi .................. C09K 11/06
2017/0357042 A1* 12/2017 Gasworth ............... C09K 11/08

FOREIGN PATENT DOCUMENTS

| CN | 104080790 A | 10/2014 |
| CN | 107001353 A | 8/2017 |
| WO | 2016046319 A1 | 3/2016 |

OTHER PUBLICATIONS

Gong, J Mater Chem A, 2015, vol. 3, 20195-20200. (Year: 2015).*
Zhou, ACS Appl Mater Interfaces, 2016, vol. 8, 31348-31358. (Year: 2016).*
Zhang, Chem Commun, 2016, vol. 52, 469-472. (Year: 2016).*
Li, Macromolecules, 2014, 4645-46520 (Year: 2014).*
Chinese First Office Action dated Apr. 21, 2023 from corresponding Chinese Patent Application No. 202080023317.0, 17 pages.
Zhou et al; "Dibenzopyran-Based Wide Band Gap Conjugated Copolymers: Structural Design and Application for Polymer Solar Cells"; ACS Applied Materials and Interfaces, vol. 8, No. 45; Oct. 24, 2016; pp. 31348-31358.
Gong et al; "Influence of polymer side chains on the photovoltaic performance of non-fullerene organic solar cells"; Journal of Materials Chemistry C, vol. 5, No., 4; Dec. 20, 2016; pp. 937-942.
Li et al; "Side Chain Influence on the Morphology and Photovoltaic Performance of 5-Fluoro-6-alkyloxybenzothiadiazole and Benzodithiophene Based Conjugated Polymers"; ACS Applied Materials and Interfaces, vol. 7, No. 20; Apr. 30, 2015; pp. 10710-10717.
Gao et al; "High-Efficiency Nonfullerene Polymer Solar Cells with Medium Bandgap Polymer Donor and Narrow Bandgap Organic Semiconductor Acceptor"; Advanced Materials, vol. 28, No. 37; Jul. 7, 2016; pp. 8288-8295.
Written Opinion Report dated Jun. 18, 2020 for PCT Appl. No. PCT/IB2020/052548.
International Search Report dated Jun. 18, 2020 for PCT Appl. No. PCT/IB2020/052548.

* cited by examiner

*Primary Examiner* — D Margaret M Seaman
(74) *Attorney, Agent, or Firm* — Ruggiero McAllister & McMahon LLC (57) ABSTRACT

Disubstituted fluoroaryloxybenzoheterodiazole compound having general formula (I):

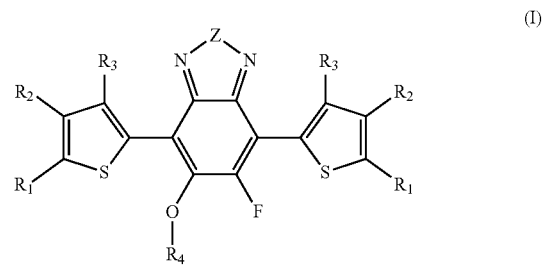

Said disubstituted fluoroaryloxybenzoheterodiazole compound having general formula (I) may be advantageously used as a spectrum converter in luminescent solar concentrators (LSCs) capable, in turn, of improving the performance of photovoltaic devices (or solar devices) selected, for example, from photovoltaic cells (or solar cells), photovoltaic modules (or solar modules), either on a rigid support, or on a flexible support.

17 Claims, 2 Drawing Sheets

DISUBSTITUTED FLUOROARYLOXYBENZOHETERODIAZOLE COMPOUNDS

CROSS-REFERENCE TO RELATED APPLICATIONS

This patent application claims priority from PCT Application PCT/IB2020/052548, which claims priority from Italian Patent Application No. 102019000004161 filed on Mar. 22, 2019, the entire disclosures of which are incorporated herein by reference.

FIELD OF THE DISCLOSURE

The present disclosure relates to a disubstituted fluoroaryloxybenzoheterodiazole compound.

More particularly, the present disclosure relates to a fluoroaryloxybenzoheterodiazole compound disubstituted with thiophenic groups.

The present disclosure also relates to a process for the preparation of said fluoroaryloxybenzoheterodiazole compound disubstituted with thiophenic groups.

The present disclosure also relates to a luminescent solar concentrators (LSCs) including at least one fluoroaryloxybenzoheterodiazole compound disubstituted with thiophenic groups, as well as to a photovoltaic device (or solar device) comprising said luminescent solar concentrators (LSCs).

DESCRIPTION OF THE RELATED ART

In the state of the art, one of the main limits to the exploitation of solar radiation energy is represented by the capability of photovoltaic devices (or solar devices) to optimally absorb only the radiations having wavelengths that fall within a narrow spectral range.

With a spectral range of solar radiation extending from wavelengths of about 300 nm to wavelengths of about 2500 nm, photovoltaic cells (or solar cells) based on crystalline silicon have, for example, an optimal absorption zone (effective spectrum) in the range 900 nm-1100 nm, while polymeric photovoltaic cells (or solar cells) are liable to damage if exposed to radiation with wavelengths lower than about 500 nm, due to phenomena of induced photodegradation which become significant below this limit. Typically, the efficiency of the photovoltaic devices (or solar devices) of the state of the art is maximum in the region of the spectrum from 570 nm to 680 nm (yellow-orange).

The aforementioned drawbacks involve a limited external quantum efficiency (EQE) of the photovoltaic devices (or solar devices), defined as the ratio between the number of electron-hole pairs generated in the semiconductor material of photovoltaic devices (or solar devices) and the number of photons that are incident on said photovoltaic devices (or solar devices).

In order to improve the external quantum efficiency (EQE) of the photovoltaic devices (or solar devices), instruments have been developed that, interposed between the source of light radiation (the sun) and the photovoltaic devices (or solar devices), selectively absorb incident radiations having wavelengths outside the effective spectrum of said photovoltaic devices (or solar devices), emitting the absorbed energy in the form of photons with a wavelength included in the effective spectrum. Said instruments are called luminescent solar concentrators (LSCs). When the energy of the photons that are re-emitted by the luminescent solar concentrators (LSCs) is higher than that of the incident photons, the photoluminescence process, including the absorption of solar radiation and the subsequent re-emission of photons at a shorter wavelength, is also called an up-conversion process. Conversely, when the energy of the photons that are emitted by the luminescent solar concentrators (LSCs) is lower than that of the incident photons, the photoluminescence process is called "down-conversion" process (or "down-shifting").

Generally, said luminescent solar concentrators (LSCs) consist of large plates of a material that is transparent to solar radiation (for example, polymeric or inorganic glasses), wherein fluorescent compounds acting as spectrum converters are dispersed, or chemically bound to said material. Due to the optical phenomenon of total reflection, the radiation emitted by the fluorescent compounds is "guided" towards the thin edges of the plate where it is concentrated on photovoltaic cells (or solar cells) placed therein. In this way, large surfaces of low-cost materials (photoluminescent plates) may be used to concentrate light on small surfaces of high-cost materials [photovoltaic cells (or solar cells)].

The fluorescent compounds may be deposited on the glass support in the form of a thin film or, as in the case of polymeric materials, they may be dispersed inside the polymeric matrix. Alternatively, the polymeric matrix may be directly functionalized with fluorescent chromophoric groups.

Ideally, to be used in spectrum converters, fluorescent compounds must have the following characteristics:

high luminescence quantum efficiency ($\Phi$) [($\Phi$) being defined according to the equation (1) below reported as the ratio between the number of photons emitted and the number of photons absorbed by a luminescent molecule per unit of time and has a maximum value equal to 1]:

$$(\Phi)=\text{number of emitted photons/number of absorbed photons} \quad (1);$$

wide absorption band in the spectral region wherein the photovoltaic device (or solar device) is poorly efficient;
high absorption coefficient;
narrow emission band in the spectral region wherein the photovoltaic device (or solar device) is more efficient;
well separated absorption and emission bands to avoid or minimize self-absorption phenomena.

It is known that some benzothiadiazole compounds, in particular 4,7-di(thien-2'-yl)-2,1,3-benzothiadiazole (DTB), are fluorescent compounds that may be used in the construction of luminescent solar concentrators (LSCs). Compounds of this type have been described, for example, in the international patent application WO 2011/048458 in the name of the Applicant.

4,7-di(thien-2'-yl)-2,1,3-benzothiadiazole (DTB) is characterized by an emission centred around 579 nm, a value which corresponds to an energy well above the minimum threshold of operation of photovoltaic cells (or solar cells), which threshold, for example, corresponds to a wavelength of about 1100 nm for the most common silicon-based photovoltaic cells (or solar cells). Moreover, its absorption of the light radiation is intense and extended over a relatively wide range of wavelengths, indicatively ranging from 550 nm (the wavelength of the green radiation) to the ultraviolet. Finally, 4,7-di(thien-2'-yl)-2,1,3-benzothiadiazole (DTB) has a Stokes' shift, in dichloromethane solution, equal to 134 nm, much higher than those of most of the commercial products so far proposed for use in luminescent solar concentrators (LSCs).

For this reason, the use of 4,7-di(thien-2'-yl)-2,1,3-benzothiadiazole (DTB) has made it possible to create luminescent solar concentrators (LSCs) of excellent quality.

However, 4,7-di(thien-2'-yl)-2,1,3-benzothiadiazole (DTB), although it absorbs a significant part of the solar spectrum, shows a modest absorption in its regions with greater wavelength, corresponding to the yellow and red radiations which, therefore, cannot be converted into others that may be more effectively exploited by the photovoltaic cell (or solar cell).

The Applicant has therefore addressed the problem of finding compounds capable of giving comparable or even greater performance, in particular in terms of power generated by the photovoltaic devices wherein they are used, with respect to known benzothiadiazole compounds.

SUMMARY OF THE DISCLOSURE

The Applicant has now found fluoroaryloxybenzoheterodiazole compounds disubstituted with thiophenic groups having a specific general formula (i.e. having general formula (I) below reported), which may be advantageously used in the construction of luminescent solar concentrators (LSCs). Said luminescent solar concentrators (LSCs) may, in turn, be advantageously used together, for example, with photovoltaic cells (or solar cells), in the construction of photovoltaic devices (or solar devices). Said disubstituted fluoroaryloxybenzoheterodiazole compounds are able to give comparable or even higher performances, in particular in terms of power generated by the photovoltaic devices wherein they are used, compared to the known benzothiadiazole compounds.

The object of the present disclosure is therefore a disubstituted fluoroaryloxybenzoheterodiazole compound having general formula (I):

(I)

wherein:
  Z represents a sulfur, oxygen, selenium atom; or a $NR_5$ group wherein $R_5$ is selected from linear or branched, preferably $C_1$-$C_8$, $C_1$-$C_{20}$ alkyl groups, or optionally substituted aryl groups;
  $R_1$, $R_2$ and $R_3$, mutually identical or different, represent a hydrogen atom; or they are selected from linear or branched, preferably $C_1$-$C_8$, $C_1$-$C_{20}$ alkyl groups, optionally containing heteroatoms, optionally substituted cycloalkyl groups, optionally substituted aryl groups, optionally substituted, linear or branched, preferably $C_1$-$C_8$, $C_1$-$C_{20}$ alkoxy groups, optionally substituted phenoxy groups, —$COOR_6$ groups wherein $R_6$ is selected from linear or branched, preferably $C_1$-$C_8$, $C_1$-$C_{20}$ alkyl groups, or it is a cyano group; provided that the substituents $R_1$ do not both represent a hydrogen atom;
  or $R_1$ and $R_2$, may optionally be bound together so as to form, together with the carbon atoms to which they are bound, a saturated, unsaturated, or aromatic, cycle or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;
  or $R_2$ and $R_3$, may optionally be bound together so as to form, together with the carbon atoms to which they are bound, a saturated, unsaturated, or aromatic, cycle or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;
  $R_4$ is selected from optionally substituted aryl groups.

Said fluoroaryloxybenzoheterodiazole compound disubstituted with thiophenic groups may be advantageously used as a spectrum converter in luminescent solar concentrators (LSCs) capable, in turn, of improving the performance of photovoltaic devices (or solar devices) selected, for example, from photovoltaic cells (or solar cells), photovoltaic modules (or solar modules), either on a rigid support, or on a flexible support.

DETAILED DESCRIPTION OF THE DISCLOSURE

For the purpose of the present description and the following claims, the definitions of the numerical intervals always comprise the extreme values unless otherwise specified.

For the purpose of the present description and the following claims, the term "comprising" also includes the terms "which essentially consists of" or "which consists of".

For the purpose of the present description and the following claims, the term "$C_1$-$C_{20}$ alkyl groups" means alkyl groups having from 1 to 20 linear or branched carbon atoms. Specific examples of $C_1$-$C_{20}$ alkyl groups are: methyl, ethyl, n-propyl, iso-propyl, n-butyl, iso-butyl, t-butyl, pentyl, 2-ethyl-hexyl, hexyl, heptyl, octyl, nonyl, decyl, dodecyl.

For the purpose of the present description and the following claims, the term "$C_1$-$C_{20}$ alkyl groups optionally containing heteroatoms" means alkyl groups having from 1 to 20 linear or branched, saturated or unsaturated, carbon atoms, wherein at least one of the hydrogen atoms is substituted with a heteroatom selected from: halogens such as, for example, fluorine, chlorine, preferably fluorine; nitrogen; sulfur; oxygen. Specific examples of $C_1$-$C_{20}$ alkyl groups optionally containing heteroatoms are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluoropentyl, perfluoroctyl, perfluorodecyl, oxymethyl, thiometyl, thioethyl, dimethylamino, propylamino, dioctylamino.

For the purpose of the present description and the following claims, the term "cycloalkyl groups" means cycloalkyl groups having from 3 to 10 carbon atoms. Said cycloalkyl groups may be optionally substituted with one or more groups, mutually identical or different, selected from: halogen atoms such as, for example, fluorine, chlorine, preferably fluorine; hydroxyl groups; $C_1$-$C_{20}$ alkyl groups; $C_1$-$C_{20}$ alkoxy groups; cyano groups; amino groups; nitro groups; aryl groups. Specific examples of cycloalkyl groups are: cyclopropyl, 1,4-dioxin, 2,2-difluorocyclopropyl, cyclobutyl, cyclopentyl, cyclohexyl, methylcyclohexyl, methoxycyclohexyl, fluorocyclohexyl, phenylcyclohexyl.

For the purpose of the present description and the following claims, the term "aryl groups" means aromatic carbocyclic groups having from 6 to 60 carbon atoms. Said aryl groups may be optionally substituted with one or more groups, mutually identical or different, selected from: halogen atoms such as, for example, fluorine, chlorine, preferably fluorine; hydroxyl groups; $C_1$-$C_{20}$ alkyl groups; $C_1$-$C_{20}$ alkoxy groups; cyano groups; amino groups; nitro groups; aryl groups. Specific examples of aryl groups are: phenyl, methylphenyl, 2,5-dimethylphenyl, 2,6-dimethylphenyl, trimethylphenyl, di-iso-propylphenyl, t-butylphenyl, methoxyphenyl, hydroxyphenyl, phenyloxyphenyl, fluorophenyl, pentafluorophenyl, chlorophenyl, nitrophenyl, dimethylaminophenyl, naphthyl, phenylnaphthyl, phenanthrene, anthracene.

For the purpose of the present description and the following claims, the term "$C_1$-$C_{20}$ alkoxy groups" means alkoxy groups having from 1 to 20 linear or branched carbon atoms. Said alkoxy groups may be optionally substituted with one or more groups, mutually identical or different, selected from: halogen atoms such as, for example, fluorine, chlorine, preferably fluorine; hydroxyl groups; $C_1$-$C_{20}$ alkyl groups; $C_1$-$C_{20}$ alkoxy groups; cyano groups; amino groups; nitro groups. Specific examples of $C_1$-$C_{20}$ alkoxy groups are: methoxyl, ethoxyl, fluoroethoxyl, n-propoxyl, iso-propoxyl, n-butoxyl, n-fluoro-butoxyl, iso-butoxyl, t-butoxyl, pentoxyl, hexyloxyl, heptyloxyl, octyloxyl, nonyloxyl, decyloxyl, dodecyloxyl.

For the purpose of the present description and the following claims, the term "phenoxy groups" means $C_6H_5O$ phenoxy groups. Said phenoxy groups may be optionally substituted with one or more groups, mutually identical or different, selected from: halogen atoms such as, for example, fluorine, chlorine, preferably fluorine; $C_1$-$C_{20}$ alkyl groups; $C_1$-$C_{20}$ alkoxy groups; cyano groups; amino groups; nitro groups. Specific examples of phenoxy groups are: phenoxyl, 4-nitro-phenoxyl, 2,4-di-nitrophenoxyl, 2-chloro-4-nitrophenoxyl, 2-fluoro-4-nitrophenoxyl, 3-fluoro-4-nitrophenoxyl, 5-fluoro-2-nitrophenoxyl, 2-aminophenoxyl.

In accordance with a preferred embodiment of the present disclosure, in said general formula (I):
Z represents a sulfur atom;
$R_1$, mutually identical, are selected from optionally substituted aryl groups, preferably are 2,6-dimethylphenyl, 2,5-dimethylphenyl, 2-phenoxyphenyl;
$R_2$ and $R_3$, mutually identical, represent a hydrogen atom;
$R_4$ is selected from optionally substituted aryl groups, preferably is phenyl.

Specific examples of compounds having general formula (I) useful for the purpose of the present disclosure are reported in Table 1.

TABLE 1

(Ia)

MPDTBOP (Ib)

PPDTBFOB (Ic)

POPDTBFOP

The present disclosure also relates to a process for the preparation of the disubstituted fluoroaryloxybenzoheterodiazole compound having general formula (I).

A further object of the present disclosure is therefore a process for the preparation of a disubstituted fluoroaryloxybenzoheterodiazole compound having general formula (I):

(I)

wherein Z, $R_1$, $R_2$, $R_3$ and $R_4$, have the same meanings described above, comprising the following steps:

(a) reacting at least one disubstituted difluorobenzoheterodiazole compound having general formula (II):

(II)

wherein Z, $R_2$ and $R_3$, have the same meanings described above, with at least one aryl alcohol having general formula (III):

$R_4$—OH            (III)

wherein $R_4$ has the same meanings described above, obtaining a disubstituted fluoroaryloxybenzoheterodiazole compound having general formula (IV):

(IV)

wherein Z, $R_2$, $R_3$ and $R_4$, have the same meanings described above;

(b) reacting the disubstituted fluoroaryloxybenzoheterodiazole compound having general formula (IV) obtained in step (a) with at least one compound selected from N-haloimides such as, for example, N-bromosuccinimide, N-bromophthalimide, N-iodosuccinimide, N-iodophthalimide, obtaining a halogenated disubstituted fluoroaryloxybenzoetherodiazole compound having general formula (V):

(V)

wherein Z, $R_2$, $R_3$ and $R_4$, have the same meanings described above and X is a halogen atom selected from bromine, iodine, preferably bromine;

(c) reacting the halogenated disubstituted fluoroaryloxybenzoheterodiazole compound having general formula (V) obtained in step (b) with at least one aryl boronic compound having general formula (VI):

(VI)

wherein $R_1$ has the same meanings described above and the substituents $R_7$ represent a hydrogen atom, or are selected from linear or branched $C_1$-$C_{10}$ alkyl groups, or from optionally substituted cycloalkyl groups, or the two $R_7$ substituents may be optionally bound together so as to form, together with the other atoms to which they are bound, a cycle as in the case of the pinacol esters of boronic acid or of the 1,3-propanediol esters of boronic acid.

In accordance with a preferred embodiment of the present disclosure, in said step (a) said disubstituted difluorobenzoheterodiazole compound having general formula (II) and said aryl alcohol having general formula (III) may be used in a 1:1 molar ratio.

In accordance with a preferred embodiment of the present disclosure, said step (a) may be carried out in the presence of at least one weak organic base which may be selected, for example, from: carboxylates of alkaline (e.g., sodium, potassium, cesium) or alkaline-earth metals (e.g., magnesium, calcium) such as, for example, potassium acetate, sodium acetate, cesium acetate, magnesium acetate, calcium acetate, potassium propionate, sodium propionate, cesium propionate, magnesium propionate, calcium propionate, or mixtures thereof; carbonates of alkaline (e.g., lithium, sodium, potassium, cesium) or alkaline-earth metals (e.g., magnesium, calcium) such as, for example, lithium carbonate, potassium carbonate, sodium carbonate, cesium carbonate, magnesium carbonate, calcium carbonate, or mixtures thereof; bicarbonates of alkaline (e.g., lithium, sodium, potassium, cesium) or alkaline-earth metals (e.g., magnesium, calcium) such as, for example, lithium bicarbonate, potassium bicarbonate, sodium bicarbonate, cesium bicarbonate, magnesium bicarbonate, calcium bicarbonate, or mixtures thereof; or mixtures thereof; preferably potassium carbonate, sodium carbonate, cesium carbonate. Preferably, said disubstituted difluorobenzoheterodiazole compound having general formula (II) and said weak organic base may be used in molar ratios ranging from 1:1 to 1:1.5, preferably ranging from 1:1 to 1:1.2.

In accordance with a preferred embodiment of the present disclosure, said step (a) may be carried out in the presence of at least one organic solvent which may be selected, for example, from: ethers such as, for example, 1,2-dimethoxyethane, 1,4-dioxane, tetrahydrofuran, or mixtures thereof; hydrocarbons such as, for example, toluene, xylene, or mixtures thereof; dipolar aprotic solvents such as, for example, N,N-dimetilformammide, N-methylpyrrolidone, dimethylsulfoxide, or mixtures thereof; or mixtures thereof; preferably N,N-dimetilformamide.

In accordance with a preferred embodiment of the present disclosure, in said step (a) said disubstituted difluorobenzoheterodiazole compound having general formula (II) may be used in said organic solvent in an amount such as to have a molar concentration in said organic solvent ranging from 0.05 M to 2 M, preferably ranging from 0.1 M to 1 M.

In accordance with a preferred embodiment of the present disclosure, said step (a) may be carried out at a temperature ranging from 60° C. to 150° C., preferably ranging from 75° C. to 100° C.

In accordance with a preferred embodiment of the present disclosure, said step (a) may be carried out for a time ranging from 1 hour to 24 hours, preferably ranging from 2 hours to 20 hours.

Generally, at the end of the aforementioned step (a) the obtained mixture, after addition of distilled water, is subjected to extraction with a chlorinated organic solvent (e.g., dichloromethane, chloroform, or mixtures thereof) obtaining an organic phase which is washed to neutral (for example, with distilled water) and anhydrified (for example, on sodium sulphate). Subsequently, the residual solvent is removed (for example, by distillation under reduced pressure) and the obtained residue is subjected to purification by means of normal laboratory techniques such as, for example, elution on a chromatographic column of silica gel; and/or organic solvent crystallisation such as, for example, hydrocarbons (e.g., n-heptane, hexane, toluene, or mixtures thereof), chlorinated solvents (e.g., dichloromethane, chloroform, or mixtures thereof), ester solvents (e.g., ethyl acetate, methyl acetate, methyl propionate, or mixtures thereof), ethereal solvents (e.g., ethyl ether, tetrahydrofuran, t-butylmethyl ether, or mixtures thereof), or mixtures thereof; and/or precipitation from alcohols (e.g., methanol, ethanol, propanol, or mixtures thereof).

In accordance with a preferred embodiment of the present disclosure, in said step (b) said disubstituted fluoroaryloxybenzoheterodiazole compound having general formula (IV) and said compound selected from N-haloimides may be used in molar ratios ranging from 1:2 to 1:3, preferably ranging from 1:2 to 1:2.5.

In accordance with a preferred embodiment of the present disclosure, said step (b) may be carried out in the presence of at least one organic solvent, preferably anhydrous, which may be selected, for example, from: ethers such as, for example, 1,2-dimethoxyethane, 1,4-dioxane, tetrahydrofuran, or mixtures thereof; chlorinated solvents such as, for example, dichloromethane, chloroform, or mixtures thereof; dipolar aprotic solvents such as, for example, N,N-dimetilformammide, N-methylpyrrolidone, dimethylsulfoxide; or mixtures thereof; preferably anhydrous tetrahydrofuran.

In accordance with a preferred embodiment of the present disclosure, in said step (b) said disubstituted fluoroaryloxybenzoheterodiazole compound having general formula (IV) may be used in said organic solvent in amounts such as to have a molar concentration in said organic solvent ranging from 0.01 M to 5 M, preferably ranging from 0.05 M to 2 M.

In accordance with a preferred embodiment of the present disclosure, said step (b) may be carried out at a temperature ranging from 20° C. to 50° C., preferably ranging from 20° C. to 30° C.

In accordance with a preferred embodiment of the present disclosure, said step (b) may be carried out for a time ranging from 1 hour to 24 hours, preferably ranging from 4 hours to 18 hours.

Generally, at the end of the aforementioned step (b) the obtained mixture, after addition of distilled water, is subjected to extraction with a chlorinated organic solvent (e.g., dichloromethane, chloroform, or mixtures thereof) obtaining an organic phase which is washed to neutral (for example, with distilled water) and anhydrified (for example, on sodium sulphate). Subsequently, the residual solvent is removed (for example, by distillation under reduced pressure) and the obtained residue is subjected to purification by means of normal laboratory techniques such as, for example, elution on a chromatographic column of silica gel; and/or organic solvent crystallisation such as, for example, hydrocarbons (e.g., n-heptane, hexane, toluene, or mixtures thereof), chlorinated solvents (e.g., dichloromethane, chloroform, or mixtures thereof), ester solvents (e.g., ethyl acetate, methyl acetate, methyl propionate, or mixtures thereof), ethereal solvents (e.g., ethyl ether, tetrahydrofuran, t-butylmethyl ether, or mixtures thereof), or mixtures thereof; and/or precipitation from alcohols (e.g., methanol, ethanol, propanol, or mixtures thereof).

For the purpose of the present disclosure, said step (c) may be carried out according to Suzuki's reaction.

In accordance with an embodiment of the present disclosure, in said step (c) said halogenated disubstituted fluoroaryloxybenzoheterodiazole compound having general formula (V) and said aryl-boronic compound having general formula (VI), may be used in molar ratios ranging from 1:2 to 1:5, preferably ranging from 1:2 to 1:4.

In accordance with a preferred embodiment of the present disclosure, said step (c) may be carried out in the presence of at least one palladium-containing catalyst which may be selected from palladium compounds in the oxidation state (0) or (II) such as, example, palladium-tetrakistrifenylphosphine [Pd(PPh$_3$)$_4$], bis-triphenylphosphine palladium dichloride [PdCl$_2$(PPh$_3$)$_2$], preferably palladium-tetrakistrifenylphosphine [Pd(PPh$_3$)$_4$]. Preferably, said halogenated disubstituted fluoroaryloxybenzoheterodiazole compound having general formula (V) and said catalyst may be used in molar ratios ranging from 1:0.15 to 1:0.01, preferably ranging from 1:0.02 to 1:0.12.

In accordance with a preferred embodiment of the present disclosure, said step (c) may be carried out in the presence of at least one weak organic base which may be selected, for example, from: carboxylates of alkaline (e.g., sodium, potassium, cesium) or alkaline-earth metals (e.g., magnesium, calcium) such as, for example, potassium acetate, sodium acetate, cesium acetate, magnesium acetate, calcium acetate, potassium propionate, sodium propionate, cesium propionate, magnesium propionate, calcium propionate, or mixtures thereof; carbonates of alkaline (e.g., lithium, sodium, potassium, cesium) or alkaline-earth metals (e.g., magnesium, calcium) such as, for example, lithium carbonate, potassium carbonate, sodium carbonate, cesium carbonate, magnesium carbonate, calcium carbonate, or mixtures thereof; bicarbonates of alkaline (e.g., lithium, sodium, potassium, cesium) or alkaline-earth metals (e.g., magnesium, calcium) such as, for example, lithium bicarbonate, potassium bicarbonate, sodium bicarbonate, cesium bicarbonate, magnesium bicarbonate, calcium bicarbonate, or mixtures thereof; or mixtures thereof; preferably potassium carbonate, sodium carbonate, cesium carbonate. In said step (b), said base may be used as it is, or in an aqueous solution. Preferably, said halogenated disubstituted fluoroaryloxybenzoetherodiazole compound having general formula (V) and said weak organic base may be used in molar ratios ranging from 1:1 to 1:20, preferably ranging from 1:2 to 1:10.

In accordance with a preferred embodiment of the present disclosure, said step (c) may be carried out in the presence of at least one organic solvent, preferably anhydrous, which may be selected, for example, from: ethers such as, for example, 1,2-dimethoxyethane, 1,4-dioxane, tetrahydrofuran, or mixtures thereof; hydrocarbons such as, for example, toluene, xylene, or mixtures thereof; dipolar aprotic solvents such as, for example, N,N-dimetilformammide, N-methylpyrrrolidone, dimethylsulfoxide, or mixtures thereof; or mixtures thereof; preferably anhydrous 1,4-dioxane. In said step (c), said organic solvent may optionally be used in a mixture with water, or in a mixture with at least one alcohol such as, for example, methanol, ethanol, n-propanol, iso-propanol, or mixtures thereof, said organic solvent and said water or said organic solvent and said at least one alcohol being used in a volumetric ratio ranging from 5:1 to 1:1, preferably ranging from 4:1 to 2:1.

In accordance with a preferred embodiment of the present disclosure, in said step (c) said halogenated disubstituted fluoroaryloxybenzoetherodiazole compound having general formula (V) may be used in said organic solvent in an amount such as to have a molar concentration in said organic solvent ranging from 0.01 M to 2 M, preferably ranging from 0.02 M to 1 M.

In accordance with a preferred embodiment of the present disclosure, said step (c) may be carried out at a temperature ranging from 50° C. to 140° C., preferably ranging from 60° C. to 120° C.

In accordance with a preferred embodiment of the present disclosure, said step (c) may be carried out for a time ranging from 2 hours to 36 hours, preferably ranging from 4 hours to 18 hours.

Generally, at the end of the aforementioned step (c) the obtained mixture, after addition of distilled water, is subjected to extraction with a chlorinated organic solvent (e.g., dichloromethane, chloroform, or mixtures thereof) obtaining an organic phase which is washed to neutral (for example, with distilled water) and anhydrified (for example, on sodium sulphate). Subsequently, the residual solvent is removed (for example, by distillation under reduced pressure) and the obtained residue is subjected to purification by means of normal laboratory techniques such as, for example, elution on a chromatographic column of silica gel; and/or organic solvent crystallisation such as, for example, hydrocarbons (e.g., n-heptane, hexane, toluene, or mixtures thereof), chlorinated solvents (e.g., dichloromethane, chloroform, or mixtures thereof), ester solvents (e.g., ethyl acetate, methyl acetate, methyl propionate, or mixtures thereof), ethereal solvents (e.g., ethyl ether, tetrahydrofuran, t-butylmethyl ether, or mixtures thereof), or mixtures thereof; and/or precipitation from alcohols (e.g., methanol, ethanol, propanol, or mixtures thereof).

The disubstituted difluorobenzoheterodiazole compounds having general formula (II) may be obtained according to processes known in the art as described, for example, by Kularatne R. S. and others in "*Journal of Materials Chemistry A*" (2013), Vol. 1(48), page 15535-15543, or by Wang N. and others in "*Journal of the American Chemical Society*" (2013), Vol. 135(45), page 17060-17068, or by Zhou H. and others in "*Angewandte Chemie International Edition*" (2011), Vol. 50(13), page 2995-2998, or are commercially available (in particular in the case wherein $R_2=R_3=$hydrogen).

Aryl alcohols having general formula (III), the N-haloimides, the aryl-boronic compounds having general formula (VI), are commercially available.

As described above, said disubstituted fluoroaryloxybenzoetherodiazole compound having general formula (I) may be advantageously used as a spectrum converter in luminescent solar concentrators (LSCs) capable, in turn, of improving the performance of photovoltaic devices (or solar devices) such as, for example, photovoltaic cells (or solar cells), photovoltaic modules (or solar modules), either on a rigid support, or on a flexible support.

Said luminescent solar concentrators (LSCs) may be prepared, for example, by melt dispersion of said disubstituted fluoroaryloxybenzoheterodiazole compound having general formula (I) in polymeric materials such as, for example, polymethylmethacrylate (PMMA), polystyrene (PS), polyvinyl acetate (PVA).

Accordingly, a further object of the present disclosure is a luminescent solar concentrator (LSC) including at least one disubstituted fluoroaryloxybenzoheterodiazole compound having general formula (I).

The disubstituted fluoroaryloxybenzoheterodiazole compound having general formula (I) may be used in said luminescent solar concentrator (LSC) in the following forms: dispersed in the polymer or in the glass, chemically bound to the polymer or glass, in solution, in the form of a gel.

For example, the luminescent solar concentrators (LSC) may contain a transparent matrix, where the term transparent matrix means any transparent material used in the form of a support, a binder, or a material wherein at least one disubstituted fluoroaryloxybenzoheterodiazole compound having general formula (I) is dispersed or incorporated. The material used for the matrix is transparent, as such, to the radiations of interest and, in particular, to the radiations having a frequency comprised in the effective spectrum of the photovoltaic device (or solar device) such as, for example, the photovoltaic cell (or solar cell) wherein it is used. Materials suitable for the purpose of the present disclosure may be therefore selected from transparent materials at least at radiations having a wavelength ranging from 250 nm to 1100 nm.

The transparent matrix which may be used for the purposes of the present disclosure may be selected, for example, from polymeric materials or vitreous materials. Said matrix is characterized by a high transparency and a high duration in relation to heat and light. Polymeric materials which may be advantageously used for the purpose of the present disclosure are, for example, polymethylmethacrylate (PMMA), epoxy resins, silicone resins, polyalkylene terephthalates, polycarbonates, polystyrene, polypropylene. Vitreous materials that may be advantageously used for the purpose of the present disclosure are, for example, silicas.

In the case wherein the matrix is of the polymeric type, said at least one disubstituted fluoroaryloxybenzoheterodiazole compound having general formula (I) may be dispersed in the polymer of said matrix by, for example, melt dispersion, and subsequent formation of a plate comprising said polymer and said at least one disubstituted fluoroaryloxybenzoheterodiazole compound having general formula (I), operating, for example, according to the technique called "casting". Alternatively, said at least one disubstituted fluoroaryloxybenzoheterodiazole compound having general formula (I) and the polymer of said matrix may be solubilized in at least one solvent obtaining a solution which is deposited on a plate of said polymer, forming a film comprising said at least one disubstituted fluoroaryloxybenzoheterodiazole compound having general formula (I) and said polymer, operating, for example, by using a "Doctor Blade" film applicator: subsequently, said solvent is allowed to evaporate.

In the case wherein the matrix is of the vitreous type, said at least one disubstituted fluoroaryloxybenzoheterodiazole compound having general formula (I) may be solubilized in at least one solvent obtaining a solution which is deposited on a plate of said matrix of the vitreous type, forming a film comprising said at least one disubstituted fluoroaryloxybenzoheterodiazole compound having general formula (I), operating, for example, by using a "Doctor Blade" type film applicator: subsequently said solvent is allowed to evaporate.

A further object of the present disclosure is a photovoltaic device (or solar device) comprising at least one photovoltaic cell (or solar cell), and at least one luminescent solar concentrators (LSC) comprising at least one disubstituted fluoroaryloxybenzoheterodiazole compound having general formula (I).

Said photovoltaic device (or solar device) may be obtained, for example, by assembling the aforesaid luminescent solar concentrator with at least one photovoltaic cell (or solar cell).

In accordance with a preferred embodiment of the present disclosure, the aforesaid solar concentrator may be made in the form of a transparent plate obtained by solubilization of said at least one disubstituted fluoroaryloxybenzoheterodiazole compound having general formula (I) and of the polymer of the matrix of the polymeric type in at least one solvent obtaining a solution which is deposited on a plate of said polymer, forming a film comprising said at least one disubstituted fluoroaryloxybenzoheterodiazole compound having general formula (I) and said polymer, operating, for example, by using of a "Doctor Blade" type film applicator: subsequently said solvent is allowed to evaporate. In said photovoltaic devices (or solar devices), said plates may be then coupled to a photovoltaic cell (or solar cell).

EXAMPLES

In order to better understand the present disclosure and to put it into practice, some illustrative and non-limiting examples thereof are reported below.

4,7-di(thien-2'-yl)-2,1,3-benzothiadiazole (DTB) was obtained as described in Example 1 of the international patent application WO 2012/007834 in the name of the Applicant, whose content is incorporated herein by reference.

Example 1

Synthesis of 6-fluoro-5-phenoxy-4,7-bis-(2-thienyl)-benzo[c]1,2,5-thiadiazole Having Formula (a) (DTBFOP)

(a)

Step (a)

In a 100 ml flask, equipped with magnetic stirring, thermometer and coolant, in an inert atmosphere, phenol (Aldrich) (163 mg; 1.73 mmoles) and potassium carbonate (Aldrich) (263 mg; 1.9 mmoles) were added to a 0.3 M solution of 4,7-di(2-thienyl)-5,6-difluoro-2,1,3-benzothiadiazole (Sunatech) (582 mg; 1.73 mmoles) in N,N-dimethylformamide (Aldrich) (6 ml): the obtained reaction mixture was heated to 82° C. and maintained, under stirring, at said temperature, for 12 hours. Subsequently, the reaction mixture was poured into distilled water (50 ml) and extracted with dichloromethane (Aldrich) (3×25 ml): the obtained organic phase was washed to neutral with distilled water (3×25 ml) and subsequently anhydrified on sodium sulphate (Aldrich). After removing most of the residual solvent by distillation under reduced pressure, the obtained residue was added, by dripping, to 50 ml of methanol, obtaining 705 mg of 6-fluoro-5-phenoxy-4,7-bis-(2-thienyl)-benzo[c]1,2,5-thiadiazole having formula (a) (DTBFOP) (yield=99%).

Example 2

Synthesis of 6-fluoro-5-phenoxy-4,7-bis-2-(5-bromothienyl)-benzo[c]1,2,5-thiadiazole having formula (b) (Br$_2$DTBFOP)

(b)

Step (b)

In a 100 ml flask, equipped with magnetic stirring, thermometer and coolant, in an inert atmosphere, N-bromosuccinimide (Aldrich) (678.7 mg; 3.83 mmoles) was added to a 0.1 M solution of 6-fluoro-5-phenoxy-4,7-bis-(2-thienyl)-benzo[c]1,2,5-thiadiazole having formula (a) (DTBFOP) obtained as described in Example 1 (705 mg; 1.72 mmoles) in anhydrous tetrahydrofuran (Aldrich) (17.2 ml): the obtained reaction mixture was kept in the dark, under stirring, at room temperature (25° C.), for 12 hours. Subsequently, the reaction mixture was poured into distilled water (50 ml) and extracted with dichloromethane (Aldrich) (3×25 ml): the obtained organic phase was washed to neutral with distilled water (3×25 ml) and subsequently anhydrified on sodium sulphate (Aldrich). After removing most of the residual solvent by distillation under reduced pressure, the obtained residue was added, by dripping, to 50 ml of methanol, obtaining 928 mg of 6-fluoro-5-phenoxy-4,7-bis-2-(5-bromothienyl)-benzo[c]1,2,5-thiadiazole having formula (b) (Br$_2$DTBFOP) (yield=95%).

Example 3

Synthesis of 6-fluoro-5-phenoxy-4,7-bis[5-(2,6-dimethylphenyl)-2-thienyl]benzo[c]-1,2,5-thiadiazole having formula (Ia) (MPDTBFOP)

MPDTBFOP

Step (c)

In a 100 ml flask, equipped with magnetic stirring, thermometer and coolant, in an inert atmosphere, 2,6-dimethylphenylboronic acid (Aldrich) (660 mg; 4.4 mmoles) and a 2 M aqueous solution of potassium carbonate (Aldrich) (1.8 g in 6.5 ml of water; 13.04 mmoles) were added to a 0.08 M solution of 6-fluoro-5-phenoxy-4,7-bis-2-(5-bromothienyl)-benzo[c]1,2,5-thiadiazole having formula (b) (Br$_2$DTBFOP) obtained as described in Example 2 (928 mg; 1.63 mmoles) in anhydrous 1,4-dioxane (Aldrich) (19.5 ml). After removing the air present by 3 vacuum/nitrogen cycles, tetrakistriphenylphosphine-palladium (Aldrich) (94.2 mg; 0.08 mmoles) was added to obtain a reaction mixture which was immersed in a bath pre-heated to 85° C. and kept, under stirring, at said temperature, for 12 hours. Subsequently, the reaction mixture was poured into distilled water (50 ml) and extracted with dichloromethane (Aldrich) (3×25 ml): the obtained organic phase was washed to neutral with distilled water (3×25 ml) and subsequently anhydrified on sodium sulphate (Aldrich). After removing most of the residual solvent by distillation under reduced pressure, the obtained residue was added, by dripping, to 100 ml of methanol, obtaining a precipitate which was recovered by filtration and subsequently purified by elution on a chromatographic column of silica gel [eluent: mixture n-heptane (Aldrich)/dichloromethane (Aldrich); ratio 9/1 (v/v)] obtaining 600 mg of 6-fluoro-5-phenoxy-4,7-bis[5-(2,6-dimethylphenyl)-2-thienyl]benzo[c]-1,2,5-thiadiazole having formula (Ia) (MPDTBFOP) (yield=60%).

Example 4

Synthesis of 6-fluoro-5-phenoxy-4,7-bis[5-(2,5-dimethylphenyl)-2-thienyl]benzo[c]-1,2,5-thiadiazole having formula (Ib) (PPDTBFOP)

PPDTBFOP

Step (c)

In a 100 ml flask, equipped with magnetic stirring, thermometer and coolant, in an inert atmosphere, 2,5-dimethylphenylboronic acid (Aldrich) (330 mg; 2.2 mmoles) and a 2 M aqueous solution of potassium carbonate (Aldrich) (900 mg in 3.2 ml of water; 6.52 mmoles) were added to a 0.08 M solution of 6-fluoro-5-phenoxy-4,7-bis-2-(5-bromothienyl)-benzo[c]1,2,5-thiadiazole having formula (b) (Br$_2$DTBFOP) obtained as described in Example 2 (464 mg; 0.82 mmoles) in anhydrous 1,4-dioxane (Aldrich) (10 ml). After removing the air present by 3 vacuum/nitrogen cycles, tetrakistriphenylphosphine-palladium (Aldrich) (47.1 mg; 0.04 mmoles) was added to obtain a reaction mixture which was immersed in a bath pre-heated to 85° C. and kept, under stirring, at said temperature, for 12 hours. Subsequently, the reaction mixture was poured into distilled water (50 ml) and extracted with dichloromethane (Aldrich) (3×25 ml): the obtained organic phase was washed to neutral with distilled water (3×25 ml) and subsequently anhydrified on sodium sulphate (Aldrich). After removing most of the residual solvent by distillation under reduced pressure, the obtained residue was added, by dripping, to 100 ml of methanol, obtaining a precipitate which was recovered by filtration and subsequently purified by elution on a chromatographic column of silica gel [eluent: mixture n-heptane (Aldrich)/dichloromethane (Aldrich); ratio 9/1 (v/v)] obtaining 456 mg of 6-fluoro-5-phenoxy-4,7-bis[5-(2,5-dimethylphenyl)-2-thienyl]benzo[c]-1,2,5-thiadiazole having formula (Ib) (PPDTBFOP) (yield=90%).

Example 5

Synthesis of 6-fluoro-5-phenoxy-4,7-bis[5-(2-phenoxyphenyl)-2-thienyl]benzo[c]-1,2,5-thiadiazole having formula (Ic) (POPDTBFOP)

POPDTBFOP

Step (c)

In a 100 ml flask, equipped with magnetic stirring, thermometer and coolant, in an inert atmosphere, 2-phenoxyphenylboronic acid (Aldrich) (165 mg; 1.1 mmoles) and a 2 M aqueous solution of potassium carbonate (Aldrich) (450 mg in 1.6 ml of water; 3.26 mmoles) were added to a 0.08 M solution of 6-fluoro-5-phenoxy-4,7-bis-2-(5-bromothienyl)-benzo[c]1,2,5-thiadiazole having formula (b) ($Br_2$ DTBFOP) obtained as described in Example 2 (232 mg; 0.41 mmoles) in anhydrous 1,4-dioxane (Aldrich) (5 ml). After removing the air present by 3 vacuum/nitrogen cycles, tetrakistriphenylphosphine-palladium (Aldrich) (23.6 mg; 0.02 mmoles) was added to obtain a reaction mixture which was immersed in a bath pre-heated to 85° C. and kept, under stirring, at said temperature, for 12 hours. Subsequently, the reaction mixture was poured into distilled water (50 ml) and extracted with dichloromethane (Aldrich) (3×25 ml): the obtained organic phase was washed to neutral with distilled water (3×25 ml) and subsequently anhydrified on sodium sulphate (Aldrich). After removing most of the residual solvent by distillation under reduced pressure, the obtained residue was added, by dripping, to 100 ml of methanol, obtaining a precipitate which was recovered by filtration and subsequently purified by elution on a chromatographic column of silica gel [eluent: mixture n-heptane (Aldrich)/dichloromethane (Aldrich); ratio 9/1 (v/v)] obtaining 216 mg of 6-fluoro-5-phenoxy-4,7-bis[5-(2-phenoxyphenyl)-2-thienyl]benzo[c]-1,2,5-thiadiazole having formula (Ic) (POPDTBFOP) (yield=70%).

Example 6 (Comparative)

6 g of polymethylmethacrylate Altuglas VSUVT 100 (PMMA) and 49.5 mg of 4,7-di(thien-2'-yl)-2,1,3-benzothiadiazole (DTB), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be ranging from 100 µm to 50 µm.

An IXYS-KXOB22-12 photovoltaic cell having a 1.2 $cm^2$ surface was then applied to one of the edges of the polymer plate.

The main face of the polymer plate [the one coated with the thin film containing 4,7-di(thien-2'-yl)-2,1,3-benzothiadiazole (DTB)] was then lit up with a light source with a power equal to 1 sun (1000 W/$m^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

Figure 1:
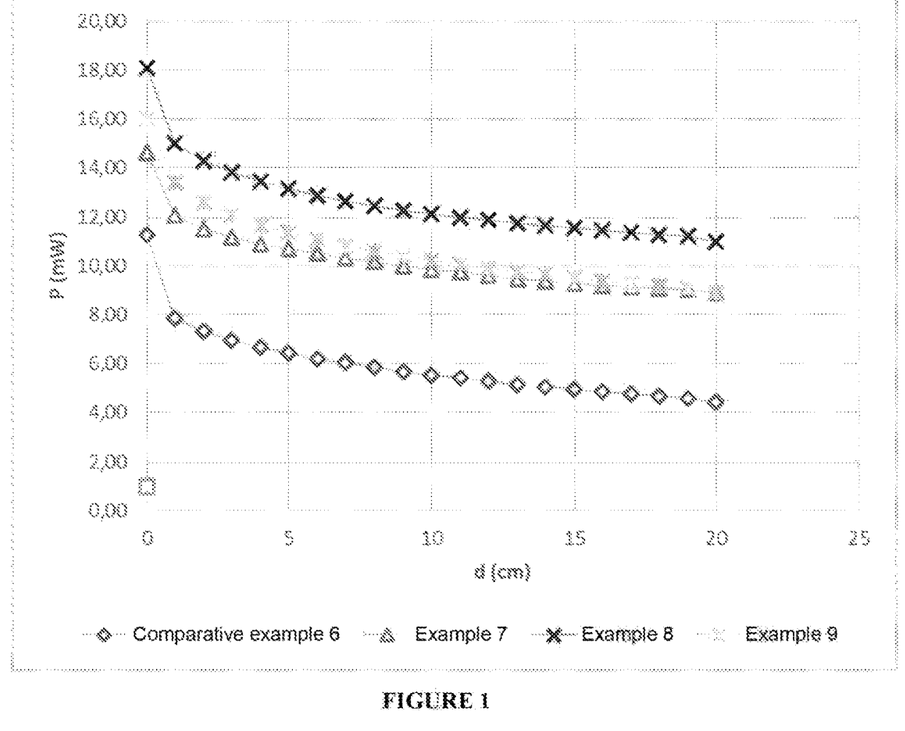
FIG. 1 shows the curve relating to the generated power value (P) expressed in mW (reported on the ordinate), as a function of the distance (d) from the edge on which the photovoltaic cell was fixed, expressed in cm (reported on the abscissa).

FIG. 1 shows the curve relating to the generated power value (P) expressed in mW (reported on the ordinate), as a function of the distance (d) from the edge on which the photovoltaic cell was fixed, expressed in cm (reported on the abscissa).

It may be seen how, in the absence of edge effects, the average power generated is equal to 5.69 mW (FIG. 1).

Figure 2:
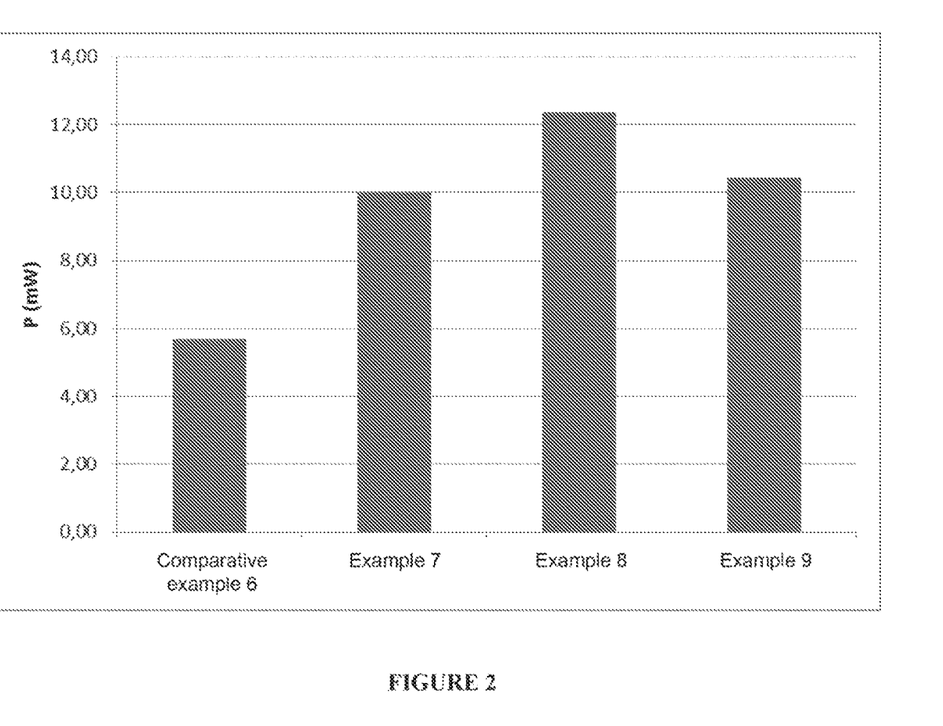
FIG. 2 shows the power value (P) generated expressed in mW (reported on the ordinate) obtained (the number of the example is reported on the abscissa).

FIG. 2 shows the power value (P) generated expressed in mW (reported on the ordinate) obtained (the number of the example is reported on the abscissa).

Example 7

6 g of polymethyl methacrylate Altuglas VSUVT 100 (PMMA) and 114.8 mg of 6-fluoro-5-phenoxy-4,7-bis[5-(2,6-dimethylphenyl)-2-thienyl]benzo[c]-1,2,5-thiadiazole having formula (Ia) (MPDTBFOP) obtained as described in Example 3, were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in red conferred by the film whose thickness was found to be ranging from 100 µm to 50 µm.

An IXYS-KXOB22-12 photovoltaic cell having a 1.2 $cm^2$ surface was then applied to one of the edges of the polymer plate.

The main face of the polymer plate [the one coated with the thin film containing 6-fluoro-5-phenoxy-4,7-bis[5-(2,6-dimethylphenyl)-2-thienyl]benzo[c]-1,2,5-thiadiazole having formula (Ia) (MPDTBFOP)] was then lit up with a light source with a power equal to 1 sun (1000 W/$m^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It may be seen how, in the absence of edge effects, the average power generated is equal to 10 mW (FIG. 1).

FIG. 2 shows the power value (P) generated expressed in mW (reported on the ordinate) obtained (the number of the example is reported on the abscissa).

Example 8

6 g of polymethyl methacrylate Altuglas VSUVT 100 (PMMA) and 110.6 mg of 6-fluoro-5-phenoxy-4,7-bis[5-(2,5-dimethylphenyl)-2-thienyl]benzo[c]-1,2,5-thiadiazole having formula (Ib) (PPDTBFOP) obtained as described in Example 4, were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in red conferred by the film whose thickness was found to be ranging from 100 m to 50 µm.

An IXYS-KXOB22-12 photovoltaic cell having a 1.2 cm² surface was then applied to one of the edges of the polymer plate.

The main face of the polymer plate [the one coated with the thin film containing 6-fluoro-5-phenoxy-4,7-bis[5-(2,5-dimethylphenyl)-2-thienyl]benzo[c]-1,2,5-thiadiazole having formula (Ib) (PPDTBFOP)] was then lit up with a light source with a power equal to 1 sun (1000 W/m²) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It may be seen how, in the absence of edge effects, the average power generated is equal to 12.36 mW (FIG. 1).

FIG. 2 shows the power value (P) generated expressed in mW (reported on the ordinate) obtained (the number of the example is reported on the abscissa).

Example 9

6 g of polymethylmethacrylate Altuglas VSUVT 100 (PMMA) and 135 mg of 6-fluoro-5-phenoxy-4,7-bis [5-(2-phenoxyphenyl)-2-thienyl]benzo[c]-1,2,5-thiadiazole having formula (Ic) (POPDTBFOP) obtained as described in Example 5, were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in red conferred by the film whose thickness was found to be ranging from 100 µm to 50 µm.

An IXYS-KXOB22-12 photovoltaic cell having a 1.2 cm² surface was then applied to one of the edges of the polymer plate.

The main face of the polymer plate [the one coated with the thin film containing 6-fluoro-5-phenoxy-4,7-bis[5-(2-phenoxyphenyl)-2-thienyl]benzo[c]-1,2,5-thiadiazole having formula (Ic) (POPDTBFOP)] was then lit up with a light source with a power equal to 1 sun (1000 W/m²) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It may be seen how, in the absence of edge effects, the average power generated is equal to 10.44 mW (FIG. 1).

FIG. 2 shows the power value (P) generated expressed in mW (reported on the ordinate) obtained (the number of the example is reported on the abscissa).

The invention claimed is:

1. Disubstituted fluoroaryloxybenzoheterodiazole compound having general formula (I):

wherein:
Z represents sulfur, oxygen, selenium; or a NR$_5$ group wherein R$_5$ is selected from linear or branched, or aryl groups optionally substituted;

R$_1$, R$_2$ and R$_3$, mutually identical or different, represent a hydrogen atom; or they are selected from linear or branched, optionally containing heteroatoms, cycloalkyl groups optionally substituted, aryl groups optionally substituted, linear or branched, alkoxy groups optionally substituted, phenoxy groups optionally substituted, —COOR$_6$ groups wherein R$_6$ is selected from linear or branched, alkyl groups, or is a cyano group; provided that the substituents R$_1$ do not both represent a hydrogen atom;

or R$_1$ and R$_2$, may optionally be bound together so as to form, together with the carbon atoms to which they are bound, a saturated, unsaturated, or aromatic, cycle or polycyclic system containing from 3 to 14 carbon atoms, optionally containing one or more heteroatoms;

or R$_2$ and R$_3$, may be optionally linked together so as to form, together with the carbon atoms to which they are bound, a saturated, unsaturated, or aromatic, cycle or polycyclic system containing from 3 to 14 carbon atoms, optionally containing one or more heteroatoms; and R4 is selected from aryl groups optionally substituted.

2. Disubstituted fluoroaryloxybenzoheterodiazole compound according to claim 1, wherein in said general formula (I):
Z represents a sulfur atom;
R1, mutually identical, are selected from € assisted-aryl groups optionally substituted;
R2 and R3, mutually identical, represent a hydrogen atom; and
R4 is selected from aryl groups optionally substituted.

3. Process for the preparation of a disubstituted fluoroaryloxybenzoheterodiazole compound having general formula (I):

(I)

wherein Z, R1, R2, R3 and R4, have the same meanings described above, comprising the following steps:
(a) reacting at least one disubstituted difluorobenzoheterodiazole compound having general formula (II):

(II)

wherein Z, R2 and R3, have the same meanings described above, with at least one aryl alcohol having general formula (III):

R4—OH (III)

wherein R4 has the same meanings described above, obtaining a disubstituted fluoroaryloxybenzoheterodiazole compound having general formula (IV):

(IV)

wherein Z, R2, R3 and R4, have the same meanings described above;

(b) reacting the disubstituted fluoroaryloxybenzoheterodiazole compound having general formula (IV) obtained in step (a) with at least one compound selected from N-haloimides, obtaining a halogenated disubstituted fluoroaryloxybenzoetherodiazol compound having general formula (V):

(V)

wherein Z, R2, R3 and R4, have the same meanings described above and X is a halogen atom selected from bromine and iodine;

(c) reacting the halogenated disubstituted fluoroaryloxy-benzoheterodiazole compound having general formula (V) obtained in step (b) with at least one aryl boronic compound having general formula (VI):

(VI)

wherein R1 has the same meanings described above and the substituents R7 represent a hydrogen atom, or are selected from linear or branched C1-C10 alkyl groups, or from cycloalkyl groups optionally substituted, or the two R7 substituents may be optionally bound together so as to form, together with the other atoms to which they are bound, a cycle as in the case of the pinacol esters of boronic acid or of the 1,3-propanediol esters of boronic acid.

4. Process for the preparation of a disubstituted fluoroaryloxybenzoheterodiazole compound having general formula (I) according to claim 3, wherein:
in said step (a) said disubstituted difluorobenzoheterodiazole compound having general formula (II) and said aryl alcohol having general formula (III) are used in a molar ratio 1:1;
said step (a) is carried out in the presence of at least one weak organic base selected from: carboxylates of alkaline or alkaline-earth metals, or mixtures thereof; carbonates of alkaline or alkaline-earth metals, or mixtures thereof; bicarbonates of alkali or alkaline-earth metals, or mixtures thereof; or mixtures thereof; said disubstituted difluorobenzoheterodiazole compound having general formula (II) and said weak organic base being used in molar ratios ranging from 1:1 to 1:1.5;
said step (a) is carried out in the presence of at least one organic solvent selected from: ethers; hydrocarbons;
in said step (a) said disubstituted difluorobenzoheterodiazole compound having general formula (II) is used in said organic solvent in an amount such as to have a molar concentration in said organic solvent ranging from 0.05 M to 2 M;

said step (a) is carried out at a temperature ranging from 60° C. to 150° C.; and said step (a) is carried out for a time ranging from 1 hour to 24 hours.

5. Process for preparation of a disubstituted fluoroaryloxybenzoheterodiazole compound having general formula (I) according to claim 3, wherein:

in said step (b) said disubstituted fluoroaryloxybenzoheterodiazole compound having general formula (IV) and said compound selected from N-haloimides are used in molar ratios ranging from 1:2 to 1:3;

said step (b) is carried out in the presence of at least one organic solvent, selected from: ethers; chlorinated solvents; dipolar aprotic solvents; or mixtures thereof;

in said step (b) said disubstituted fluoroaryloxybenzoheterodiazole compound having general formula (IV) is used in said organic solvent in an amount such as to have a molar concentration in said organic solvent ranging from 0.01 M to 5 M, said step (b) is carried out at a temperature ranging from 20° C. to 50° C.; and said step (b) is carried out for a time ranging from 1 hour to 24 hours.

6. Process for the preparation of a disubstituted fluoroaryloxybenzoheterodiazole compound having general formula (I) according to claim 3, wherein:

said step (c) is carried out according to the Suzuki's reaction;

in said step (c), said halogenated disubstituted fluoroaryloxybenzoheterodiazole compound having general formula (V) and said aryl boronic compound having general formula (VI), are used in molar ratios ranging from 1:2 to 1:5;

said step (c) is carried out in the presence of at least one palladium-containing catalyst selected from palladium compounds in an oxidation state (0) or (II); said halogenated disubstituted fluoroaryloxybenzoheterodiazole compound having general formula (V) and said catalyst being used in molar ratios ranging from 1:0.15 to 1:0.01;

said step (c) is carried out in the presence of at least one weak organic base selected from: carboxylates of alkaline or alkaline-earth metals, or mixtures thereof; carbonates of alkaline or alkaline-earth metals, or mixtures thereof; bicarbonates of alkaline or alkaline-earth metals, or mixtures thereof; or mixtures thereof; said base being used as such, or in aqueous solution; said halogenated disubstituted fluoroaryloxybenzoheterodiazole compound having general formula (V) and said weak organic base being used in molar ratios ranging from 1:1 to 1:20;

said step (c) is carried out in the presence of at least one organic solvent, selected from: ethers; hydrocarbons; dipolar aprotic solvents; or mixtures thereof; said organic solvent being optionally used in a mixture with water, or in a mixture with at least one alcohol, said organic solvent and said water or said organic solvent and said at least one alcohol being used in a volume ratio ranging from 5:1 to 1:1;

in said step (c) said halogenated disubstituted fluoroaryloxy-benzoheterodiazole compound having general formula (V) is used in said organic solvent in an amount such as to have a molar concentration in said organic solvent ranging from 0.01 M to 2 M;

said stage (c) is carried out at a temperature ranging from 50° C. to 140° C.; and said stage (c) is carried out for a time ranging from 2 hours to 36 hours.

7. Luminescent solar concentrator (LSC) including at least one disubstituted fluoroaryloxybenzoheterodiazole compound having general formula (I) according to claim 1.

8. Photovoltaic device (or solar device) comprising at least one photovoltaic cell (or solar cell), and at least one luminescent solar concentrator (LSC) according to claim 7.

9. Disubstituted fluoroaryloxybenzoheterodiazole compound according to claim 1, wherein $R_5$ is selected from linear or branched, $C_1$-$C_{20}$ alkyl groups;

wherein $R_1$, $R_2$ and $R_3$ are selected from linear or branched, $C_1$-$C_{20}$ alkyl groups, optionally containing heteroatoms or linear or branched, $C_1$-$C_{20}$ alkoxy groups optionally substituted;

wherein $R_6$ is selected from linear or branched, $C_1$-$C_{20}$ alkyl groups;

wherein $R_1$ and $R_2$, may optionally be bound together so as to form, together with the carbon atoms to which they are bound, a saturated, unsaturated, or aromatic, cycle or polycyclic system containing from 4 to 6 carbon atoms, optionally containing one or more heteroatoms selected from the group consisting of oxygen, sulfur, nitrogen, silicon, phosphorus, and selenium; and wherein $R_2$ and $R_3$, may be optionally linked together so as to form, together with the carbon atoms to which they are bound, a saturated, unsaturated, or aromatic, cycle or polycyclic system containing from 4 to 6 carbon atoms, optionally containing one or more heteroatoms selected from the group consisting of oxygen, sulfur, nitrogen, silicon, phosphorus, and selenium.

10. Disubstituted fluoroaryloxybenzoheterodiazole compound according to claim 9, wherein $R_5$ is selected from linear or branched, $C_1$-$C_8$ alkyl groups; wherein $R_1$, $R_2$ and $R_3$ are selected from linear or branched, $C_1$-$C_8$ alkyl groups, optionally containing heteroatoms;

wherein $R_1$, $R_2$ and $R_3$ are selected from linear or branched, $C_1$-$C_8$ alkyl groups, optionally containing heteroatoms or linear or branched, $C_1$-$C_8$ alkoxy groups optionally substituted;

wherein $R_6$ is selected from linear or branched, $C_1$-$C_8$ alkyl groups;

wherein $R_1$ and $R_2$, may optionally be bound together so as to form, together with the carbon atoms to which they are bound, a saturated, unsaturated, or aromatic, cycle or polycyclic system containing from 4 to 6 carbon atoms, optionally containing one or more heteroatoms selected from the group consisting of oxygen, sulfur, nitrogen, silicon, phosphorus, and selenium; and wherein $R_2$ and $R_3$, may be optionally linked together so as to form, together with the carbon atoms to which they are bound, a saturated, unsaturated, or aromatic, cycle or polycyclic system containing from 4 to 6 carbon atoms, optionally containing one or more heteroatoms selected from the group consisting of oxygen, sulfur, nitrogen, silicon, phosphorus, and selenium.

11. Disubstituted fluoroaryloxybenzoheterodiazole compound according to claim 2, wherein $R_1$ is selected from the group consisting of 2,6-dimethylphenyl, 2,5-dimethylphenyl and 2-phenoxyphenyl; and wherein $R_4$ is phenyl.

12. Disubstituted fluoroaryloxybenzoheterodiazole compound according to claim 3, wherein X is bromine, and wherein N-haloimides selected from the group consisting of N-bromosuccinimide, N-bromophthalimide, N-iodosuccinimide, and N-iodophthalimide.

13. Disubstituted fluoroaryloxybenzoheterodiazole compound according to claim 4,
  wherein said at least one weak organic base is selected from the group consisting of potassium carbonate, sodium carbonate, and cesium carbonate;
  wherein said weak organic base is used in molar ratios ranging from 1:1 to 1.2;
  wherein ethers are selected from the group consisting of 1,2-dimethoxyethane, 1,4-dioxane, tetrahydrofuran, and mixtures thereof;
  wherein hydrocarbons are selected from the group consisting of toluene, xylene, dipolar aprotic solvents, and mixtures thereof;
  wherein in said step (a) said disubstituted difluorobenzoheterodiazole compound is used in said organic solvent in an amount such as to have a molar concentration in said organic solvent ranging from 0.1 M to 1 M;
  wherein said step (a) is carried out at a temperature ranging from 75° C. to 100° C.; and
  wherein said step (a) is carried out for a time ranging from 2 hours to 20 hours.

14. Disubstituted fluoroaryloxybenzoheterodiazole compound according to claim 13, wherein the aprotic solvents are selected from the group consisting of N,N-dimethylformamide, N-methylpyrrolidone, and dimethylsulfoxide.

15. Disubstituted fluoroaryloxybenzoheterodiazole compound according to claim 5,
  wherein in said step (b) said disubstituted fluoroaryloxybenzoheterodiazole compound having general formula (IV) and said compound selected from N-haloimides are used in molar ratios ranging from 1:2 to 1:2.5;
  wherein in said step (b) said at least one organic solvent is anhydrous;
  wherein ethers are selected from the group consisting of 1,2-dimethoxyethane, 1,4-dioxane, tetrahydrofuran, and mixtures thereof;
  wherein chlorinated solvents are selected from the group consisting of dichloromethane, chloroform, and mixtures thereof;
  wherein dipolar aprotic solvents are selected from the group consisting of N,N-dimethylformamide, N-methylpyrrolidone, dimethylsulfoxide; and mixtures thereof;
  wherein in said step (b) said disubstituted fluoroaryloxybenzoheterodiazole compound having general formula (IV) is used in said organic solvent in an amount such as to have a molar concentration in said organic solvent ranging from 0.05 M and 2 M;
  wherein said step (b) is carried out at a temperature ranging from 20° C. to 30° C.; and
  wherein said step (b) is carried out for a time ranging from 4 hours to 18 hours.

16. Disubstituted fluoroaryloxybenzoheterodiazole compound according to claim 15, wherein said ethers is anhydrous tetrahydrofuran.

17. Disubstituted fluoroaryloxybenzoheterodiazole compound according to claim 6,
  wherein in said step (c), said halogenated disubstituted fluoroaryloxybenzoheterodiazole compound having general formula (V) and said aryl boronic compound having general formula (VI) are used in molar ratios ranging from 1:2 to 1:4;
  wherein said step (c) is carried out in the presence of said at least one palladium-containing catalyst selected from the group consisting of palladium-tetrakistrifenylphosphine [$Pd(PPh_3)_4$] and bis-triphenylphosphine palladium dichloride [$PdCl_2(PPh_3)_2$];
  wherein said halogenated disubstituted fluoroaryloxybenzoheterodiazole compound having general formula (V) and said catalyst are used in molar ratios ranging from 1:0.02 to 1:0.12;
  said step (c) is carried out in the presence of at least one weak organic base selected from potassium carbonate, sodium carbonate, and cesium carbonate;
  wherein said halogenated disubstituted fluoroaryloxybenzoheterodiazole compound having general formula (V) and said weak organic base being used in molar ratios ranging from 1:2 to 1:10;
  wherein in said step (c) said at least one organic solvent is anhydrous;
  wherein said ethers are selected from the group consisting of 1,2-dimethoxyethane, 1,4-dioxane, tetrahydrofuran, and mixtures thereof;
  wherein said hydrocarbons are selected from the group consisting of toluene, xylene, and mixtures thereof;
  wherein dipolar aprotic solvents are selected from the group consisting of N,N-dimethylformamide, N-methylpyrrolidone, dimethylsulfoxide, and mixtures thereof;
  wherein said at least one alcohol is selected from the group consisting of methanol, ethanol, n-propanol, iso-propanol, and mixtures thereof;
  wherein said organic solvent and said water or said organic solvent and said at least one alcohol are used in a volume ratio ranging from 4:1 to 2:1;
  wherein in said step (c), said halogenated disubstituted fluoroaryloxy-benzoheterodiazole compound having general formula (V) is used in said organic solvent in an amount such as to have a molar concentration in said organic solvent ranging from 0.02 M to 1 M;
  wherein said stage (c) is carried out at a temperature ranging from 60° C. and 120° C.; and
  wherein said stage (c) is carried out for a time ranging from 4 hours to 18 hours.

* * * * *